United States Patent
Takahashi et al.

(10) Patent No.: US 6,939,894 B2
(45) Date of Patent: Sep. 6, 2005

(54) METHODS FOR REDUCING EXCESSIVE BARKING OF A DOG

(75) Inventors: Michio Takahashi, Kawasaki (JP);
Makoto Bannai, Kawasaki (JP);
Shinobu Seki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/176,609

(22) Filed: Jun. 24, 2002

(65) Prior Publication Data

US 2003/0018027 A1 Jan. 23, 2003

(30) Foreign Application Priority Data

Jun. 29, 2001 (JP) .................................. 2001-197612

(51) Int. Cl.[7] ................... A61K 31/197; A61K 31/662
(52) U.S. Cl. ........................... 514/567; 514/114
(58) Field of Search ................. 514/567, 114

(56) References Cited

U.S. PATENT DOCUMENTS

| 4,975,430 A | 12/1990 | Jahr et al. ........... 514/255 |
| 5,762,960 A | 6/1998 | Dodman ............. 424/451 |
| 6,380,176 B2 | 4/2002 | Takahashi et al. .......... 514/114 |

FOREIGN PATENT DOCUMENTS

| EP | 1 138 332 | 10/2001 |
| WO | WO 99/45906 | 9/1999 |

OTHER PUBLICATIONS

Crowell–Davis, S., Proc. Cent. Vet. Conf. (1999 Meeting, 104–107).*
T. Yokawa, et al. "The Ventromedial Nucleus of the Hypothalamus Outputs Long–Lasting Running in Rats," Physiology & Behavior, vol. 46, 1989, pp. 713–717.
Takashi Yokawa, et al. "Hyper–Running Activity Originating From the Hypothalamus is Blocked by GABA," Physiology & Behavior, vol. 47, 1990, pp. 1261–1264.
Kazumi Narita, et al. "Interaction Between Excitatory and Inhibitory Amino Acids in the Ventromedial Nucleus of the Hypothalamus in Inducing Hyper–Running" Brain Research, vol. 603, 1993, pp. 243–247.
Soraya V. Juarbe–Diaz, "Assessment and Treatment of Excessive Barking in the Domestic Dog" Progress in Companion Animal Behavior, vol. 27, No. 3, May 1997, pp. 515–532.
W. A. Hewlett, Psychiatric Annals, vol. 23, No. 6, XP–008002601, pp. 309–316, "The Use of Benzodiazepines in Obsessive Compulsive Disorder and Tourette's Syndrome", Jun. 1993.

* cited by examiner

Primary Examiner—Phyllis G. Spivack
(74) Attorney, Agent, or Firm—Oblon, Spivak, McClelland, Maier & Neustadt, P.C.

(57) ABSTRACT

Methods for reducing excessive barking of a dog are disclosed wherein GABA or SKF97541 is administered.

23 Claims, 1 Drawing Sheet

METHODS FOR REDUCING EXCESSIVE BARKING OF A DOG

BACKGROUND OF THE INVENTION

The present invention relates to a pharmaceutical composition and a method for preventing non-intentional problem behaviors, such as a stereotyped behavior, behaviors caused by separation anxiety, behaviors caused by OCD (obsessive-compulsive disorder). Particularly, the present invention relates to a pharmaceutical composition and a method of preventing excessive barking of companion animals.

In companion animals, problem behaviors, for example, excessive barking of dogs or scratching behaviors to damage skin, has been a controversial problem from various point of view. However, it has not been clearly elucidated why such behaviors occur, for example, why dogs bark. Generally, barking is a normal and natural communication mean for dogs, and it is known that the native causes of barking of dogs are, for example, internal requirements to solve struggles such as the requirement to prevent intruders to their territories, instinctive desires, and appearance of anxiety or struggle. However, the cause of barking is not specified in many cases, and there are many cases where it should be admitted that they are barking non-intentionally.

As a solution for this, methods have generally been adopted where excessive barking is prevented by training. Such methods include methods of punishment by, for example, a water pistol or a can with pebbles or ultrasonic beam. There are also approaches by hitting dogs or shouting at dogs, which may enhance undesired behaviors of dogs and which would be unsuccessful. On the other hand, it is also contrive to control the excessive barking or stereotyped behaviors of companion animals by using special devices. As an examples, the product, Aboistop$^R$ (Dynavet, France) are referred to as an efficient device in that dogs would seek the location of citronellal order released from the device and, as a result, dogs may be distracted. However, this device is not necessarily effective in some cases such as the case where the dogs are barking from anxiety (for example, in the case of separation anxiety disorder). Furthermore, a training to acclimatize the dog to this device before using Aboistop$^R$, or a labor to provide a toy, a person to stay with the dog while your are not at home or a partner dog is also required.

Additionally, a collar which automatically triggers an electrical shock to is widely sold except in England. This collar inflicts a shock circuit through a microphone if the dog barks. The use of this device is not desirable, because the device is recognized as atrocious and is unsuccessful in many cases and also because there is a possibility of significantly injuring the comfort level of dogs.

Furthermore, some veterinarians prescribe Clomipramine or monoamine oxidase inhibitors as a drug having an anxiolytic effect, but these are not effective in many cases. For example Clomipramine is believed to have reduced effectiveness in the case of excessive barking. Monoamine oxidase inhibitors are originally the drugs used for treatment of depression in human, of which efficacy are not confirmed in companion animals and also should not be use in symptomatic treatment.

Finally, the process where the vocal cord is excised may be recommended, but this is like a final process and is not desirable. Actually, most veterinarians in Europe do not accept this process.

On the other hand, independent of the foregoing clinical investigations, many attempts have been made focused on the running activity, especially on the night running activity, during the studies of neuron. For example, the inventors of the present invention reported that when the ventromedial nucleus of hypothalamus (hereinafter simply referred to as "VMH") of rat was stimulated by water absorbent polymers, the running activity on rat was induced by the pressure stimulus (Yokawa, et. al., Physiology & behavior (1989), 46, 713–717). According to this report, signals from VMH were indicated to be required for the induction of running activity in rat, based on the observation that the running activity did not occur when VMH region had been excised from the animals. Additionally, the inventors demonstrated that the foregoing induction of rat running activity caused by polymers could be inhibited by administration of GABA (γ-aminobutyric acid) (Yokawa, et. al., Physiol. & Behav. (1990), 47, 1261–1264).

The inventors also reported that the running activity in rat might be induced by a kind of ionotropic glutamate receptor, kainate receptor agonists (Narita, et. al., Brain Res. (1993), 603, 243–247). According to the report, the running activity in rat was induced by kainate and was not inhibited by GABA but the running activity was inhibited by DNQX (6,7-dinitroquinoxaline-2,3-dione), a kainate receptor antagonist, which suggest that the neuron controlling the running activity in rat may be stimulated through kainate receptors and that $GABA_A$ receptors presynaptically inhibit the neuron controlling the running activity in rat against the kainate receptors. On the other hand, for $GABA_B$ receptors, it has been also reported that substances having the competitive inhibitory activity against $GABA_B$ receptors are likewise useful in treatment of neurological disease accompanied by convulsion, Alzheimer's disease or memory retention disorder (Japanese unexamined publication, JP 4-243853).

SUMMARY OF THE INVENTION

The object of the present invention is to provide a pharmaceutical composition and a method for preventing non-intentional problem behaviors of animals (except for human beings), especially of companion animals.

More specifically, the object of the present invention is to provide a pharmaceutical composition and a method for preventing stereotyped behaviors, behaviors cased by separation anxiety and behaviors caused by OCD in companion animals.

Particularly, the object of the present invention is to provide a pharmaceutical composition and a method of preventing excessive barking of companion animals.

The inventors have been suggested that there are some neurons in the VMH which were strongly suggested to be involved in the running activity in rat, especially in the night running activity, as previously mentioned. The inventors designated the neuron existing in the VMH region as "running neuron" and concluded that the running neuron is the neuron which regulate the non-intentional locomotion in rat. In rats, running neuron exists in VMH as above-described, the hypothalamic region, including the VMH, is believed to be a lower central and well conserved among vertebrates. Therefore, the inventors believe that the running neuron exist also in other vertebrate animals, including humans and canine. Furthermore, the inventors became to believe that the running neuron must exists in vertebrates such as human and dog, and to associate the input from the neuron with excessive barking, repeated behaviors such as stereotyped behaviors, from the point of view that problem behaviors of companion animals including, for example, stereotyped behaviors, behaviors caused by separation anxiety, behaviors caused by OCD, especially excessive barking as a problem behavior, are "non-intentional behaviors" similar of the locomotion of rats. Additionally, the inventors led to invent the pharmaceutical composition and the method by suppressing input from running neuron, which may inhibit problem behaviors such as stereotyped behaviors, behaviors caused by separation anxiety, behaviors caused by OCD or excessive barking, but do not inhibit intentional locomotion.

Thus, the present invention is a pharmaceutical composition or a method for preventing problem behaviors such as stereotyped behaviors, behaviors caused by separation anxiety, behaviors cause by OCD or excessive barking of animals (except for human beings), which comprises a substance being able to inhibit the running neuron in the presynaptic or postsynaptic manner. Particularly, the present invention is a pharmaceutical composition for preventing problem behaviors such as stereotyped behaviors, behaviors caused by separation anxiety, behaviors cause by OCD and especially excessive barking of animals (except for human beings), which comprises a substance selected from the group consisting of $GABA_B$ receptor agonists, $GABA_A$ receptor agonists, or substances that enhance the activity of $GABA_A$ receptor and kainate receptor antagonists, or any combination thereof. The present invention is also a method of preventing problem behaviors such as stereotyped behaviors, behaviors caused by separation anxiety and behaviors cause by OCD, especially excessive barking of animals (except for human beings) by administrating such pharmaceutical compositions.

DESCRIPTION OF THE PREFERRED EMBODIMENTS

Figure 1:
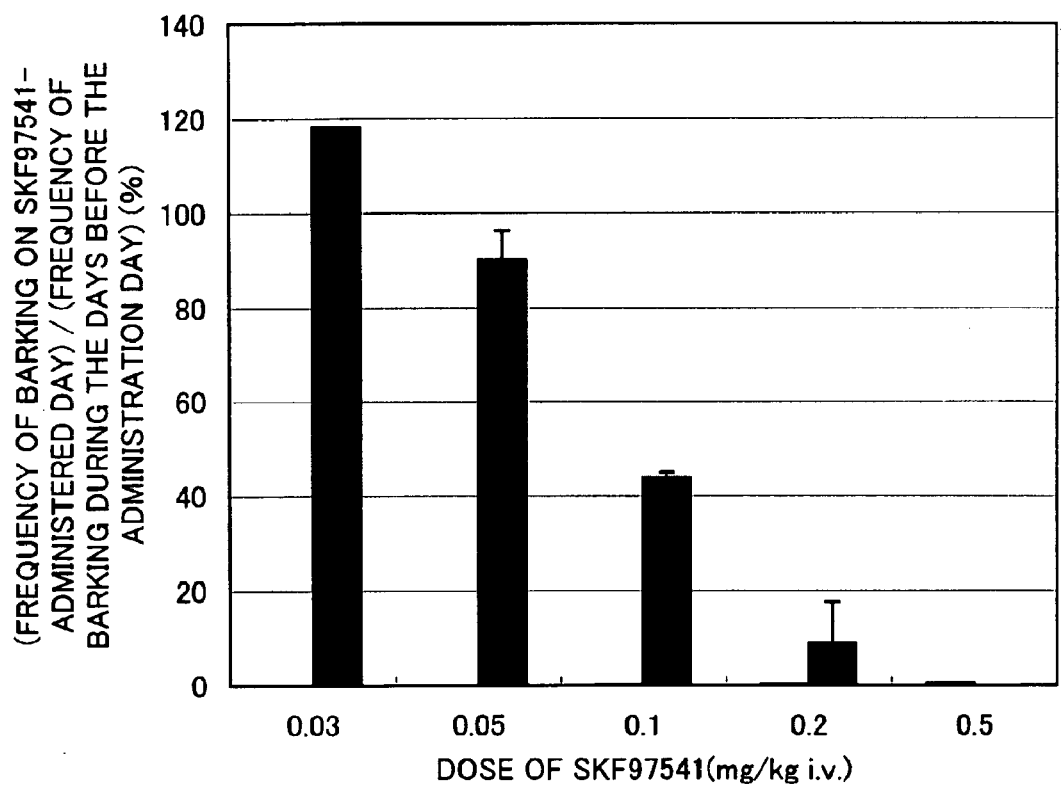
FIG. 1 shows the dose-dependent effect of admistrating SKF97541 ($GABA_B$ receptor agonist on excessive barking. The values are presented by mean values and standard errors.

The pharmaceutical composition and method of the present invention can be applied to non-intentional problem behaviors including stereotyped behaviors, behaviors caused by separation anxiety, behaviors caused by OCD in animals having running neuron, for example, general vertebrates, especially companion animals.

"Companion animal" as used herein refers to the animals according to the definition of, for example, "Bailliere's Comprehensive Verterinary Dictionary", 1988, Bailliere Thindall), that is, "the animal including dog, cat, horse, little bird, mouse, marmot and other exotic animal species, which is fed by human as a companion, as a fun, as a psychological support, as a garnish for presenting to others or as an existent possessing a function to be shared by all human with non-human animals, which do not disturb the emotional or psychological meriority of human and which is a companion behaving faithfully in most cases" (supra). These animals may be generally fed as "pets". Particularly, "companion animal" as used herein is vertebrates, preferably mammalian. Companion animals include dog, cat, horse, mouse, and marmot. The term "companion animal" is the term used for explaining the kind of animals, and is not intended to limit the particular purpose or situation where animals are actually fed. Thus, for example, dog is not always intended to be merely fed such as in the case of a guide dog or a service dog, but dog is still a companion animal since it may also be fed as a pet in many cases.

"Problem behavior" as used herein generally refers to a behavior when the behavior affords an adverse effect to the animal, other animals or human. However, it includes behaviors which deviate from the usual behaviors for the animal, even if the behaviors are not actually adverse for the animal, other animals or human. The problem behaviors include stereotyped behaviors, behaviors caused by separation anxiety, behaviors caused by OCD.

"Stereotyped behavior" as used herein refers to a pattern of behavior which repeatedly occurs with no purpose for the animal, that is, with any purpose or function which can be apparently recognized. For example, it includes excessive barking, continuous wondering, incessant licking of the forelimbs, tail-chasing behavior, gyrating movement, bobbing the head and the like. These behavior patterns are etiologically believed to be identical.

"Behaviors caused by separation anxiety" as used herein refers to the behaviors which are adverse to the owner and which occurs when the animal is left alone. The behaviors caused by separation anxiety include barking, digging the ground, chewing something, excreting behavior at the place where it is forbidden, and the like.

"Behaviors cause by OCD (obsessive compulsive disorder)" as used herein refers to the behavior of reacting improperly to a triggering stimulus bringing repeated and ceremonial asyndetic behavior patterns.

"Excessive barking" as used herein refers to the behavior where a dog excessively barks. Excessive barking may derive from stereotyped behaviors, separation anxiety or OCD.

Generally, problem behaviors caused by a companion animal are those which may be problems for the owner to live a social life with the animal, as described above. Among companion animals, problem behaviors of dog are greatly interested and excessive barking as one of the non-intentional problem behaviors may become a cause of arising a social problem. As previously mentioned, one type of excessive barking is the separation anxiety, which is known as a behavior where a dog repeats excessive barking on separation from the owner. This behavior is believed to be different from the behavior of barking as required, such as in the case when a stranger is encountered.

The present invention relates to a method of preventing only non-intentional problem behaviors of companion animals, such as excessive barking of dogs.

More specifically, the present invention is suitable to prevent non-intentional behaviors of companion animals, especially to prevent excessive barking or stereotyped behaviors.

Additionally, "animal" does not include human beings when the term is use in association with "problem behavior" or with the similar concept thereof, even if it is not explicitly indicated.

The pharmaceutical composition and the method of the present invention may be used for non-intentional problem behaviors of animals in general, in particular, they may be preferably used for preventing excessive barking, stereotyped behaviors and the like.

Running neuron inhibitory substances which may be included in the pharmaceutical composition of the present invention and which can be used in the present invention include $GABA_B$ receptor agonists, $GABA_A$ receptor agonists, $GAGA_A$ receptor enhancers (substances which can affect $GABA_A$ receptors and can enhance the activity the receptors), kainate receptor antagonist and any combination thereof.

Particularly, running neuron inhibitory substances may include, but are not limited to: GABA, isoguvacine (1,2,3,6-tetrahydro-4-pyrydinecarboxylic acid), muscimol (5-aminomethyl-3-hydroxyisoxazole), THIP (4,5,6,7-tetrahydroisoxazolo [5,4-c]pyridine-3-ol) and the like as $GABA_A$ receptor agonists; GABA, baclofen (4-amino-3-(4-chlorophenyl) butanoic acid), SKF97541 (3-aminopropyl (methyl)phosphinic acid) and the like as $GABA_B$ receptor agonists; benzodiazepine and the like as $GABA_A$ receptor enhancers; and CNQX (6-cyano-7-nitroquinoxaline-2,3-dione), CNQX disodium salt (6-cyano-7-nitroquinoxaline-2,3-dione disodium), DNQX, GAMS ($\gamma$-D-glutamylamino methylsulphonic acid), NBQX (2,3-dioxo-6-nitro-1,2,3,4-tetrahydrobenzo[f]quinoxaline-7-sulphonamide), NBQX disodium (2,3-dioxo-6-nitro-1,2,3,4-tetrahydorbenzo[f] quinoxaline-7-sulphonamide disodium) and the like as kainite receptor antagonists.

To determining whether the given substance has the running neuron inhibitory activity, a bioassay system can be used. For example, a 26-gauge stainless guide cannula may be implanted in rat VMH and Rats are allowed at least for seven days for the surgical recovery. After recovery period, about 100 pmol of kinate in about 0.5 $\mu l$ saline is injected through the internal cannula to ascertain that the guide cannula position hits the running neuron. The rats that do not express running behavior, which means that they do not respond to the treatment, will be omitted from the following experiments. Three days later, the mixture of kinate (about 100 pmol) and the putative inhibitory compound (about 50 pmol to about 50 nmol) may be injected through the cannula. When the compound injected simultaneously with kainate either reduces or abolishes the kinate-induced running activity, that compound can be recognized as the running neuron inhibitory substance.

The pharmaceutical composition of the present invention may be administered orally or parenterally, preferably orally. Parenteral administration includes transcutaneous administration, intravenous infusion and intraperitoneal administration. The dose may be determined depending on the age of the patient, condition of a disease, general condition, body weight, therapeutic plan and desired effects and the like. The pharmaceutical composition of the present invention may be administered as a dose per day such that the amount of the effective component or the running neuron-inhibitory substance ranges from about 1 mg/kg body weight to about 500 mg/kg body weight, preferably about 10 mg/kg body weight to about 50 mg/kg body weight for oral administration, and ranges from preferably about 0.001 mg/kg body weight to about 1 mg/kg body weight and more preferably about 0.01 mg/kg body weight to about 0.1 mg/kg body weight for parenteral administration.

The pharmaceutical composition of the present invention is generally administered to a patient over 1 to 6 times a day and preferably 1 to 3 times a day. The pharmaceutical composition of the present invention may continuously be administered over a long period of time. If a problem behavior appears at a specific time or during a specific period, however, the pharmaceutical composition may be administered over limited number of times at the specific points of time or during the specific periods depending on the intensity of the symptom. In any case, if other therapeutic agents or other therapies are used simultaneously, the dose of the pharmaceutical composition of the present invention is adjusted depending on the amounts and characteristic properties of these agents and therapies. If the pharmaceutical composition of the present invention is orally administered, the composition may be used in the conventional formulations such as syrup and suspension. The pharmaceutical composition may be preferably introduced into foods or drinking water. In such cases, the frequency of the administration may be identical with that of feeding, generally about once to twice a day (1–2/day).

The pharmaceutical composition of the present invention may further comprise pharmaceutically acceptable excipients. If necessary, the pharmaceutical composition of the present invention may additionally comprise aromatics, colorants, disintegrators, preservatives for stabilization, suspending agents, emulsifying agents and lubricants. If the pharmaceutical composition of the invention is parenterally administered, the osmotic pressure thereof may be adjusted, if necessary. Pharmaceutically and physiologically acceptable substances can be used as the excipients or the additional substances and the specific examples thereof are sugars such as lactose and galactose; starches such as cornstarch; fatty acid salts such as magnesium stearate, alginic acid, talc and polyethylene glycol. The pharmaceutical composition of the present invention may also contain any other substances which are suitable for animal feeding stuff.

The pharmaceutical composition of the present invention comprises the running neuron inhibitory substances as the effective component in an amount ranging from about 1 to 95% by weight and preferably about 10 to about 80% by weight on the basis of the total weight of the composition. The rate of the running neuron inhibitory substances may be chosen depending on factors such as the formulations of the pharmaceutical composition of the present invention, the desired effects to be achieved and the total amount of the pharmaceutical composition to be administered. In particular, if the pharmaceutical composition of the present invention is orally administered, the composition comprises the running neuron inhibitory substances as the effective component thereof in an amount ranging from 1 to 95% by weight, preferably 10 to 80% by weight, more preferably 20 to 70% by weight and particularly preferably about 20 to about 60% by weight on the basis of the total weight of the pharmaceutical composition. If the pharmaceutical composition is parenterally administered, it generally comprises the running neuron inhibitory substances in an amount ranging from about 0.01 to 30% by weight and preferably 0.05 to 20% by weight on the basis of the total weight of the pharmaceutical composition. In any case, if the pharmaceutical composition of the invention comprises a plurality of running neuron inhibitory substances, the amount of the individual running neuron inhibitory substance may be controlled depending on the effect thereof.

The pharmaceutical composition of the present invention may be generally applied to animals (except human beings), for example, dogs, cats or cattles such as bovine or porcine, especially dogs, which may arise problem behaviors including stereotyped behaviors, behaviors caused by separation anxiety and behaviors caused by OCD.

EXAMPLES

Example 1

Two ovariectomized healthy female beagles (10 kg) of 2 years old were used for the following experiments.

The experiments was performed for seven (7) days as one cycle and the data were recorded, which were repeated for 3 months (12 cycles). The data were statistically processed. The experimental dogs were fed in a room which was equipped with an air conditioner keeping 22° C. During the first 6 days, the animals were fed with 400 g of food (Science Diet Maintenance, dry, Japan Hills Colgate) at 4 o'clock every day. Water was freely provided. The animals were habituated in the experimental cages. The seventh ($7^{th}$) day in each cycle, the condition was kept except that the indicated amount of SKF97541 GABA$_B$ receptor agonist) was intravenously administrated at 2 o'clock P.M. The frequency of barking during 5 minutes before feeding was recorded every day by a video camera. The ratio of the frequency of barking on the day where the animals were received SKF97541 to the mean values of the barking frequency during the first 6 days where the animals were not received SKF97541 is indicated as percentages in Table 1 and FIG. 1. In the experiment, no notable point regarding to the general symptom of animals was observed.

TABLE 1

Effects of administration of SKF97541 (GABA$_A$ receptor agonist) on excessive barking

| Amount of administrated SKF97541 | 0.025 | 0.05 | 0.1 | 0.2 | 0.5 |
|---|---|---|---|---|---|
| (frequency of barking on the administrated day)/ (frequency of barking on non-administrated days) | 118.2 ± 0.0 | 90.2 ± 6.2 | 44.0 ± 1.1 | 8.8 ± 8.8 | 0 |

Example 2

The following experiment was performed by using an 11 years old Pomeranian (4.5 kg weight) in which a symptom of separation anxiety was confirmed.

The experimental animal was fed in a room which was equipped with an air conditioner keeping 22° C. and were provided with 200 g of canned dog food (Science Diet Maintenance, beef can, Japan Hills Colgate) twice per day in the morning and in the evening. Water was freely provided. The animals had been habituated in the experimental cages before recording the frequency of excessive barking with a set up video camera. Excessive barking during 30 minutes after every one left the room was recorded for 2 days. The barking frequency on day 1 was 178 times and 203 times on day 2. At 6 o'clock P.M. on the treatment day, above-mentioned canned dog food mixed with 150 mg of powdered GABA was fed and the barking frequency during 30 minutes after every one left the room was recorded. The barking frequency for that recording was 0 (zero).

Instead of GABA, SKF97541 was also intravenously administrated at the amount of 0.05 mg/kg body weight or 0.1 mg/kg body weight and the barking frequency was recorded in a similar manner. The result was that the dog did not bark in both cases.

Again, no notable point regarding to the general symptom of animals was observed in this experiment.

The present invention provides a pharmaceutical composition and a method for preventing non-intentional behaviors of animals including stereotyped behaviors, behaviors cause by separation anxiety and behaviors cause by OCD. More specifically, non-intentional behaviors of companion animals, particularly excessive barking, can be prevented by the present invention. Especially, excessive barking of dogs deriving from separation anxiety, which is frequently observed, can be effectively prevented.

What is claimed is:

1. A method of reducing excessive barking of a dog inneed thereof, comprising administrating a pharmaceutical composition comprising at least one compound selected from the group consisting of GABA and SKF97541.

2. The method of claim 1, wherein said compound is GABA.

3. The method of claim 1, wherein said compound is SKF97541.

4. The method of claim 1, wherein said administering is orally.

5. The method of claim 4, wherein said at least one substance is administered at a total dose per day ranging from about 1 mg/kg body weight to about 500 mg/kg body weight.

6. The method of claim 4, wherein said at least one substance is administered at a total dose per day ranging from about 10 mg/kg body weight to about 50 mg/kg body weight.

7. The method of claim 4, wherein said at least one substance comprises 1 to 95% by weight of said pharmaceutical composition.

8. The method of claim 4, wherein said at least one substance comprises 10 to 80% by weight of said pharmaceutical composition.

9. The method of claim 4, wherein said at least one substance comprises 20 to 70% by weight of said pharmaceutical composition.

10. The method of claim 4, wherein said at least one substance comprises 20 to 60% by weight of said pharmaceutical composition.

11. The method of claim 1, wherein said administering is parenterally.

12. The method of claim 11, wherein said at least one substance is administered at a total dose per day ranging from about 0.001 mg/kg body weight to about 1 mg/kg body weight.

13. The method of claim 11, wherein said at least one substance is administered at a total dose per day ranging from about 0.01 mg/kg body weight to about 0.1 mg/kg body weight.

14. The method of claim 11, wherein said at least one substance comprises 0.01 to 30% by weight of said pharmaceutical composition.

15. The method of claim 11, wherein said at least one substance comprises 0.05 to 20% by weight of said pharmaceutical composition.

16. The method of claim 11, wherein said administering is selected from the group consisting of transcutaneous administration, intravenous infusion and intraperitoneal administration.

17. The method of claim 1, wherein said pharmaceutical composition is administered 1 to 6 times per day.

18. The method of claim 1, wherein said pharmaceutical composition is administered 1 to 3 times per day.

19. The method of claim 1, wherein said pharmaceutical composition is administered 1 to 2 times per day.

20. The method of claim 1, wherein said pharmaceutical composition further comprises at least one additive selected from the group consisting of an aromatic, a colorant, a disintegrator, a preservative for stabilization, a suspending agent, an emulsifying agent and a lubricant.

21. The method of claim 1, wherein said pharmaceutical composition further comprises at least one pharmaceutically acceptable excipient.

22. The method of claim 21, wherein said pharmaceutically acceptable excipient is selected from the group consisting of a sugar, a starch, and a fatty acid salt.

23. The method of claim 1, wherein said pharmaceutical composition further comprises one or more compound selected from the group consisting of baclofen, isoguvacine, muscimol, and THIP.

* * * * *